United States Patent
Cree

(10) Patent No.: US 10,821,622 B2
(45) Date of Patent: Nov. 3, 2020

(54) EXTRUSION COATED PERFORATED NONWOVEN WEB AND METHOD FOR MAKING

(71) Applicant: James W. Cree, Loveland, OH (US)

(72) Inventor: James W. Cree, Loveland, OH (US)

(73) Assignee: ADVANTAGE CREATION ENTERPRISE LLC, Loveland, OH (US)

(*) Notice: Subject to any disclaimer, the term of this patent is extended or adjusted under 35 U.S.C. 154(b) by 175 days.

(21) Appl. No.: 15/842,968

(22) Filed: Dec. 15, 2017

(65) Prior Publication Data

US 2018/0104842 A1 Apr. 19, 2018

Related U.S. Application Data

(62) Division of application No. 12/971,879, filed on Dec. 17, 2010, now Pat. No. 9,849,602.

(Continued)

(51) Int. Cl.
*B32B 3/24* (2006.01)
*B26F 1/20* (2006.01)
(Continued)

(52) U.S. Cl.
CPC .............. *B26F 1/20* (2013.01); *A61F 13/5121* (2013.01); *B26F 1/24* (2013.01); *B26F 1/26* (2013.01);
(Continued)

(58) Field of Classification Search
CPC .............. B32B 3/266; Y10T 428/24281; A61F 13/5121
See application file for complete search history.

(56) References Cited

U.S. PATENT DOCUMENTS

| 3,719,736 A | 3/1973 | Woodruff |
| 3,881,489 A | 5/1975 | Hartwell |

(Continued)

FOREIGN PATENT DOCUMENTS

| CN | 1705464 | 12/2005 |
| DE | 197 50 459 | 5/1999 |

(Continued)

OTHER PUBLICATIONS

Pre-Examination Office Action dated May 20, 2019, in related Brazilian Application No. BR112012014968-7 filed Jun. 18, 2012 (4 pages) with Google machine translation (4 pages).

(Continued)

*Primary Examiner* — William P Watkins, III
(74) *Attorney, Agent, or Firm* — Donald E. Hasse; Hasse & Nesbitt LLC

(57) ABSTRACT

A method for making an extrusion coated perforated nonwoven web. The method comprises the steps of extruding a molten polyethylene coating onto a nonwoven web, and aperturing the molten polyethylene coating through heat and pneumatic pressure differential to create microperforations therein at a density of between about 35 and about 120 perforations per linear inch. The resulting microperforated nonwoven web is then thermomechanically perforated by feeding it through perforating rolls, at least one of which has raised protuberances to create macroperforations that extend through at least the polyethylene coating. The macroperforations have a density of between about 6 and about 35 perforations per linear inch. The perforated nonwoven web is useful as a topsheet for absorbent articles.

14 Claims, 2 Drawing Sheets

Related U.S. Application Data

(60) Provisional application No. 61/287,961, filed on Dec. 18, 2009.

(51) Int. Cl.

| | | |
|---|---|---|
| *A61F 13/512* | (2006.01) | |
| *B26F 1/24* | (2006.01) | |
| *B26F 1/26* | (2006.01) | |
| *B32B 3/26* | (2006.01) | |
| *B32B 3/30* | (2006.01) | |
| *B32B 5/26* | (2006.01) | |
| *B32B 27/08* | (2006.01) | |
| *B32B 27/12* | (2006.01) | |
| *B32B 27/20* | (2006.01) | |
| *B32B 27/32* | (2006.01) | |
| *B32B 38/04* | (2006.01) | |
| *B32B 37/15* | (2006.01) | |
| *B32B 38/18* | (2006.01) | |

(52) U.S. Cl.
CPC ............. *B32B 3/266* (2013.01); *B32B 3/30* (2013.01); *B32B 5/26* (2013.01); *B32B 27/08* (2013.01); *B32B 27/12* (2013.01); *B32B 27/20* (2013.01); *B32B 27/32* (2013.01); *B32B 38/04* (2013.01); *B32B 37/153* (2013.01); *B32B 38/1858* (2013.01); *B32B 2038/047* (2013.01); *B32B 2305/20* (2013.01); *B32B 2323/04* (2013.01); *B32B 2555/02* (2013.01); *Y10T 428/24281* (2015.01); *Y10T 428/24322* (2015.01); *Y10T 428/24331* (2015.01)

(56) References Cited

U.S. PATENT DOCUMENTS

| | | | |
|---|---|---|---|
| 3,957,414 A | 5/1976 | Bussey, Jr. et al. | |
| 4,128,679 A | 12/1978 | Pohland | |
| 4,223,063 A | 9/1980 | Sabee | |
| 4,276,336 A | 6/1981 | Sabee | |
| 4,285,100 A | 8/1981 | Schwarz | |
| 4,609,518 A | 9/1986 | Curro et al. | |
| 4,629,643 A | 12/1986 | Curro et al. | |
| 4,780,352 A | 10/1988 | Palumbo | |
| 4,886,632 A | 12/1989 | Van Iten et al. | |
| 4,950,264 A | 8/1990 | Osborn, III | |
| 4,995,930 A | 2/1991 | Merz et al. | |
| 5,009,653 A | 4/1991 | Osborn, III | |
| 5,158,819 A | 10/1992 | Goodman, Jr. et al. | |
| 5,336,545 A | 8/1994 | Morman | |
| 5,368,909 A | 11/1994 | Langdon et al. | |
| 5,383,869 A | 1/1995 | Osborn, III | |
| 5,399,174 A | 3/1995 | Yeo et al. | |
| 5,418,045 A | 5/1995 | Pike et al. | |
| 5,422,172 A | 6/1995 | Wu | |
| 5,494,736 A | 2/1996 | Willey et al. | |
| RE35,206 E | 4/1996 | Hassenboehler, Jr. et al. | |
| 5,567,376 A | 10/1996 | Turi et al. | |
| 5,575,786 A | 11/1996 | Osborn, III | |
| 5,591,149 A | 1/1997 | Cree et al. | |
| 5,626,571 A | 5/1997 | Young et al. | |
| 5,656,119 A | 8/1997 | Srinivasan et al. | |
| 5,674,211 A | 10/1997 | Ekdahl | |
| 5,674,216 A | 10/1997 | Buell et al. | |
| 5,693,037 A | 12/1997 | Lee et al. | |
| 5,695,377 A | 12/1997 | Triebes et al. | |
| 5,814,389 A | 9/1998 | Giacometti | |
| 5,851,935 A | 12/1998 | Srinivasan et al. | |
| 5,882,769 A | 3/1999 | McCormack et al. | |
| 5,997,986 A | 12/1999 | Turi et al. | |
| 6,015,764 A | 1/2000 | McCormack et al. | |
| 6,069,097 A | 5/2000 | Suzuki et al. | |
| 6,106,925 A | 8/2000 | Palumbo | |
| 6,190,602 B1 | 2/2001 | Blaney et al. | |
| 6,228,462 B1 | 5/2001 | Lee et al. | |
| 6,286,145 B1 | 9/2001 | Welchel et al. | |
| 6,300,257 B1 | 10/2001 | Kirchberger et al. | |
| 6,353,149 B1 | 3/2002 | Stone | |
| 6,376,095 B1 | 4/2002 | Yunwa et al. | |
| 6,395,211 B1 | 5/2002 | Dettmer et al. | |
| 6,537,644 B1 | 3/2003 | Kauschke et al. | |
| 6,610,904 B1 | 8/2003 | Thomas et al. | |
| 6,700,036 B2 | 3/2004 | Thomas et al. | |
| 6,703,115 B2 | 3/2004 | Hale et al. | |
| 6,720,279 B2 | 4/2004 | Cree et al. | |
| 6,752,947 B1 | 6/2004 | Lanigan et al. | |
| 6,849,319 B2 | 2/2005 | Cree et al. | |
| 6,942,896 B1 | 8/2005 | Martin | |
| 6,942,748 B2 | 9/2005 | Cree et al. | |
| 7,037,569 B2 | 5/2006 | Curro et al. | |
| 7,204,907 B2 | 4/2007 | Cree et al. | |
| 7,476,632 B2 | 1/2009 | Olson et al. | |
| 7,625,829 B1 | 12/2009 | Cree et al. | |
| 7,695,799 B2 | 4/2010 | Cree | |
| 7,713,683 B2 | 5/2010 | Gray et al. | |
| 8,182,728 B2 | 5/2012 | Cree et al. | |
| 8,241,543 B2 | 8/2012 | O'Donnell et al. | |
| 2002/0098341 A1 | 7/2002 | Schiffer et al. | |
| 2002/0160085 A1 | 10/2002 | Tokita et al. | |
| 2003/0017345 A1 | 1/2003 | Middlesworth et al. | |
| 2003/0125688 A1 | 7/2003 | Keane et al. | |
| 2003/0225383 A1 | 12/2003 | Glaug et al. | |
| 2004/0005457 A1 | 1/2004 | Delucia et al. | |
| 2004/0121687 A1 | 6/2004 | Morman et al. | |
| 2004/0161586 A1 | 8/2004 | Cree et al. | |
| 2005/0106980 A1 | 5/2005 | Abed et al. | |
| 2005/0124251 A1 | 6/2005 | Tsai et al. | |
| 2005/0214506 A1 | 9/2005 | Lee et al. | |
| 2005/0241750 A1 | 11/2005 | McCormack et al. | |
| 2006/0087053 A1 | 4/2006 | O'Donell et al. | |
| 2006/0234586 A1 | 10/2006 | Wong et al. | |
| 2007/0029694 A1* | 2/2007 | Cree .................... A61F 13/537 264/156 |
| 2007/0048498 A1 | 3/2007 | Cree | |
| 2007/0123124 A1 | 5/2007 | Middlesworth et al. | |
| 2007/0237924 A1 | 10/2007 | Bruce et al. | |
| 2007/0249253 A1 | 10/2007 | Angeli et al. | |
| 2007/0250026 A1 | 10/2007 | Venturino et al. | |
| 2007/0250031 A1* | 10/2007 | Woltman .......... A61F 13/5514 604/385.201 |
| 2007/0259154 A1 | 11/2007 | Cree | |

FOREIGN PATENT DOCUMENTS

| | | |
|---|---|---|
| DE | 100 08 827 | 9/2001 |
| EP | 0164740 | 12/1985 |
| EP | 0360929 | 4/1990 |
| EP | 0749739 B1 | 11/2000 |
| EP | 1712667 A1 | 10/2006 |
| GB | 2 282 990 | 4/1995 |
| WO | 92/00050 | 1/1992 |
| WO | 98/55295 A1 | 12/1998 |
| WO | 99/65673 | 12/1999 |
| WO | 00/04215 A2 | 1/2000 |
| WO | 2004/007158 | 1/2004 |
| WO | 2004/058121 | 7/2004 |
| WO | 2008051548 A2 | 5/2008 |

OTHER PUBLICATIONS

PCT/US2010/061084 PCT International Search Report and Written Opinion dated Sep. 8, 2011 on corresponding PCT application (11 pages).

PCT—IPRP—PCT/US2010/061084 PCT International Preliminary Report on Patentability dated Jun. 28, 2012 on corresponding PCT application (7 pages).

PCT—ISRWO—PCT/US2010/000860 PCT International Search Report and Written Opinion dated Jun. 22, 2010 on corresponding PCT application (6 pages).

(56) References Cited

OTHER PUBLICATIONS

PCT—IPRP—PCT/US2010/000860 PCT International Preliminary Report on Patentability dated Oct. 6, 2011 on corresponding PCT application (6 pages).
EP—ESR—EP 10 838 305 EP Communication dated Jan. 27, 2014 (1 page) with attached Supplemental European Search Report dated Jan. 16, 2014 (3 pages). (4 total pages).
CN—CN 201080022321.1 First Office Action dated Dec. 27, 2013 (8 pages) with English translation (11 pages). (19 pages total).
EP—EP 10756471.8—EP Communication dated Jun. 17, 2014 (1 page) with attached Supplemental European Search Report dated Jun. 6, 2014 (6 pages). (7 total pages).
Cree, U.S. Appl. No. 11/468,044, filed Aug. 29, 2006.
Cree, U.S. Appl. No. 12/362,740, filed Jan. 30, 2009.
Cree, U.S. Appl. No. 12/971,879, filed Dec. 17, 2010.
Cree, U.S. Appl. No. 13/259,334, filed Sep. 23, 2011.
Cree, U.S. Appl. No. 14/695,263, filed Apr. 24, 2015.
First Office Action dated Aug. 20, 2019, in related Brazilian Application No. BR112012014968-7 filed Jun. 18, 2012 (4 pages) with Google machine translation (5 pages).

* cited by examiner

EXTRUSION COATED PERFORATED NONWOVEN WEB AND METHOD FOR MAKING

CROSS-REFERENCE TO RELATED APPLICATION

This application is a divisional of U.S. application Ser. No. 12/971,879, filed Dec. 17, 2010, which claims the benefit of U.S. Provisional Application No. 61/287,961, filed Dec. 18, 2009, the disclosures of which are incorporated herein by reference.

TECHNICAL FIELD

The present invention relates to an extrusion coated, perforated nonwoven web that has a raised textured porous coating that provides a soft, drapable and non-sticky feel, and a method for making such webs.

BACKGROUND OF THE INVENTION

Apertured nonwoven webs are used in various industrial and consumer products sectors. For example, apertured nonwoven webs are used to produce disposable sheets, disposable garments, filtration masks and hygiene and sanitary products, such as sanitary napkins, incontinence pads and baby diapers.

Apertured nonwovens can be manufactured using various techniques. One technique entails obtaining a thermobonded or spunbonded nonwoven and aperturing the nonwoven using a set of raised needles as described in U.S. Pat. Nos. 4,128,679 and 4,886,632.

Apertured nonwovens intended for use as absorbent article topsheets that exhibit one way, valve-like behaviour can be created by laminating a plastic sheet of film prepared using traditional extrusion techniques (for example, a thin sheet of LDPE delivered through a cast or blown extrusion head) and aperturing the film and nonwoven combination using solid forming techniques known in the art (e.g., calendar perforation of laminates as described in U.S. Pat. No. 4,780,352). Laminates generated by joining or aligning a formed film and a nonwoven can be perforated by mechanical techniques as described in U.S. Pat. No. 7,204,907.

Another technique for creating apertured webs, particularly fiber based apertured webs, uses thermomechanical contact perforation such as pin perforation or an engraved cylinder that is in contact with a smooth cylinder, as described in U.S. Pat. Nos. 5,814,389, 4,128,679 and 4,886,632. Yet another technique for creating a web uses a vacuum apertured laminate as described in U.S. Pat. No. 4,995,930.

Current apertured webs used in absorbent articles as the skin contacting cover layer such as a topsheet, are limited in their ability to be skin soft, discrete (quiet), moldable to the skin, and/or absorbent of fluid to maintain a dry feeling and convey the sensation of dryness. Laminates of film and nonwoven as described above, especially in U.S. Pat. No. 4,995,930, uses nonwoven fiber as the skin facing material to deliver softness benefits. However when such laminates are wet, the fiber cover retains the fluid and the film material has no ability to drain the fibrous nonwoven matrix. The user's body may develop a skin rash as a result of the adjacent topsheet moisture. Such a laminate may also be noisy when the wearer is walking because it lacks flexibility to mold to the body since it cannot be prepared with a low basis weight (e.g., less that 27 gsm). In addition, such a laminate is expensive since it requires purchasing and combining a plastic film with the nonwoven material. As a consequence, the laminate and/or product made using the laminate may be stiff, noisy, and scratchy or provide a generally unpleasant or wetness sensation.

SUMMARY OF THE INVENTION

The present invention relates to a method for making an extrusion coated, perforated nonwoven web, comprising extruding a molten polyethylene coating having a basis weight between about 7 and about 17 gsm onto a nonwoven web having a basis weight between about 9 and about 40 gsm, aperturing said molten polyethylene coating through heat and pneumatic pressure differential to create microperforations therein at a density of between about 35 and about 120 perforations per linear inch to provide a microperforated nonwoven web, thermomechanically perforating said microperforated nonwoven web by feeding it through perforating rolls, at least one of said perforating rolls having raised protuberances to create macroperforations therein that extend through at least the polyethylene coating, said macroperforations having a density of between about 6 and about 35 perforations per linear inch.

The present invention also relates to an extrusion coated, perforated nonwoven web made by the above method, and an absorbent articles comprising a topsheet made of the perforated nonwoven web.

DETAILED DESCRIPTION OF THE INVENTION

The present invention relates to an extrusion coated, perforated nonwoven web useful as a topsheet for an absorbent article. The product is made by first extruding and aperturing a polyethylene coating onto a nonwoven web to form microperforations therein that have the appearance of raised small conical apertures applied to the side of the nonwoven web that will face the wearer's skin. In one embodiment, the extrusion coating is a layered combination of a polyethylene blend comprising inert filler particles that help retain the raised texture of the nonwoven web after it undergoes a second thermomechanical perforating step. In one example, the polyethylene blend is physically extruded at a low weight level onto the surface of a perforated drum while applying a pressure differential, such as described in U.S. Pat. No. 4,995,930, to perforate the molten polyethylene coating while almost simultaneously adhering a porous fiber-like nonwoven web by a-combination of contact and vacuum pressure to the molten polyethylene before it has the chance to cool down. The resulting microperforated, coated nonwoven web is then subjected to a second aperturing step that creates macroperforations therein that extend at least through the coating layer of the nonwoven web.

Figure 1:
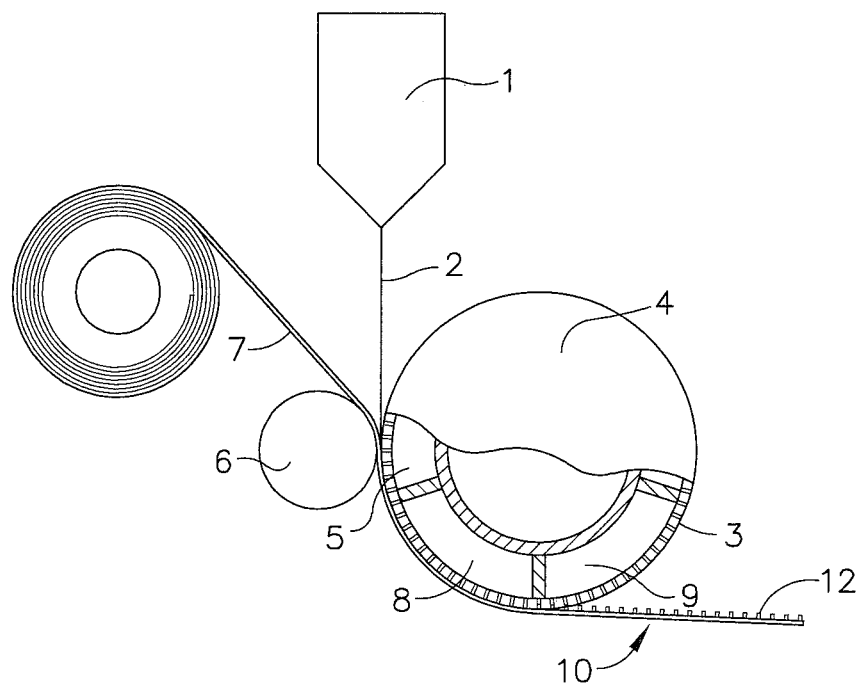
FIG. 1 shows a method for extruding a molten polyethylene coating onto a nonwoven web while aperturing the coating to create microperforations therein.

FIG. 1 shows a method for extruding a molten polyethylene coating onto a nonwoven web while aperturing the coating to create microperforations therein. In FIG. 1, a thin molten polyethylene layer 2 is fed from extruder die 1 onto the sievelike surface 3 of a cylinder or drum 4. A vacuum chamber 5, which subjects the polyethylene layer to a pneumatic vacuum, is located inside the cylinder 4 at the point where the polyethylene layer meets the cylinder 4. With the help of a guide roller 6, a fibrous nonwoven web 7 is fed onto the sievelike surface 3 at the same time as the polyethylene layer. The pneumatic vacuum exerted by vacuum chamber 5 sucks sections of the polyethylene layer into the openings in the sievelike surface, forming projections and perforating the layer within these projections. Air is sucked through the fibrous nonwoven web 7 and presses the web against the polyethylene layer as well as cooling the layer at the same time. The guide roller 6 can help in this pressing operation, but this is not necessary to bond the polyethylene layer to the web as a coating. Two other vacuum chambers 8 and 9 are located in cylinder 4. Vacuum chamber 8 sucks in air to cool the microperforated nonwoven web 10, while vacuum chamber 9 cools the sievelike surface 3.

In the above method, the polyethylene coating has a basis weight between about 7 and about 17 gsm, typically between about 10 and about 15 gsm, e.g., between about 14 and 16 gsm. In one embodiment, the polyethylene coating is a two layer blend, typically an A/B layered blend with the B layer adjacent to the nonwoven side having a polymeric composition that can help the layered coating stick to the nonwoven. The A layer will have an easy-to-rupture or perforate polymeric composition. Both layers can be microperforated by the vacuum process described in U.S. Pat. No. 4,995,930, incorporated herein by reference.

The nonwoven web may be any porous web that has a fibrous appearance. Nonwoven webs can be made by various processes using carded fibers that are thermally bonded, airthrough bonded, or directly extruded via a process called spunbond or meltblown. The nonwoven web has a basis weight between about 9 gsm and about 40 gsm, typically between about 10 and about 30 gsm, e.g., between about 10 and about 16 gsm. The nonwoven fibers are predominantly polyethylene or polypropylene, or blends thereof. The nonwoven typically is hydrophilic, or it can be a layered airthrough nonwoven with the side facing the absorbent core being more hydrophilic than the side that contacts the microperforated coating. In one embodiment, the nonwoven has a capillary gradient such that capillaries closer to the absorbent core are smaller than ones adjacent the coating layer. The nonwoven layer facing the core may have higher affinity to fluid, which can be created by using a more permanent hydrophilic material that lowers the contact angle of the web or by using capillary channeled fibers.

In one embodiment, the molten polyethylene coated web is apertured with a pressure differential to exhibit raised three dimensional volcano-like perforations such as described in U.S. Pat. No. 6,228,462, incorporated herein by reference, extending outward away from the nonwoven layer. These volcano-like perforations, such as microperforations 12 shown in FIGS. 1-4, create the feel of a fiber like surface. When an absorbent article topsheet is made from the perforated nonwoven web herein, it is desirable to have such apertured cones pointing toward the wearer side of the article to enhance the comfort sensation. The microperforations 12 have a density between about 35 and about 120 perforations per linear inch, typically from about 45 to about 80 perforations per linear inch. The cone-like apertures appear somewhat inverted in FIG. 4 with the largest diameter being at the interface between the polyethylene film 2 and the nonwoven web 7.

In one embodiment, a thin molten polyethylene layer having A/B layers, where the B layer is predominantly polyethylene and the A layer contains between 2% and 30% by weight filler particles, is co-extruded onto a drum having a supporting screen such as the sievelike surface shown in FIG. 1, and pneumatically formed at the same time the polyethylene layer contacts a support carrier layer of a hydrophilic thermobonded nonwoven web. The nonwoven web may have an aggressive fluid transportation mechanism such as shaped fibers. As mentioned above, the polyethylene layer may comprise co-extruded layers with the layer adjacent the supporting screen comprising LDPE that is easy to rupture.

The filler particles in the polyethylene coating may be organic or inorganic filler particles, such as described in U.S. Patent Application Publication 2002/0098341 A1, incorporated herein by reference. Suitable inorganic fillers include calcium carbonate, clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide, and combinations thereof. Suitable organic fillers include particles made of polystyrene, polyamides, polyvinyl alcohol, polyethylene oxide, polyethylene terephthalate, polybutylene terephthalate, polycarbonate, polytetrafluoroethylene, and other suitable polymers and derivatives thereof. The mean diameter for the filler particles should range from about 0.1-10 microns, typically about 0.5-7.0 microns, e.g., about 0.8-2.0 microns.

Figure 2:
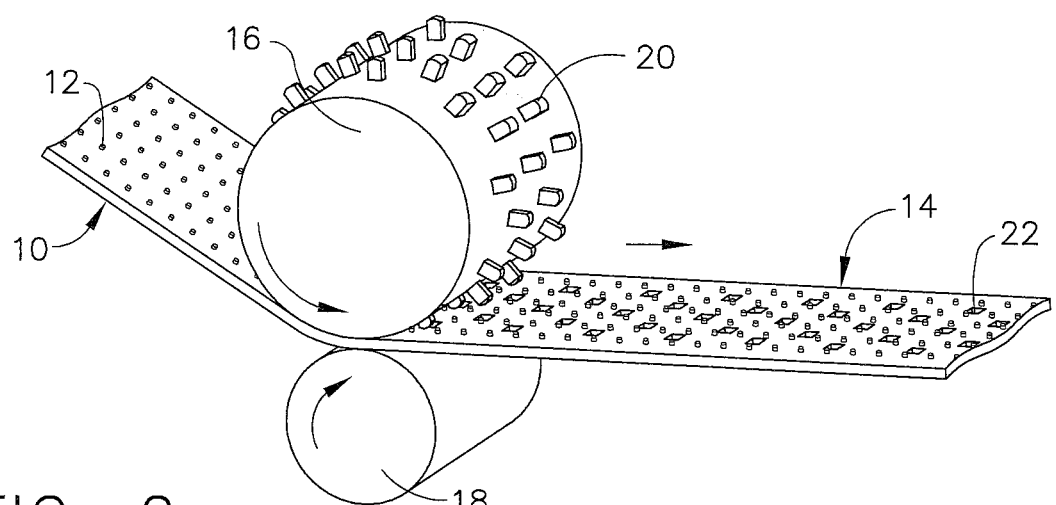
FIG. 2 shows a method for thermomechanically perforating the nonwoven web made using the method shown in FIG. 1 to create macroperforations therein.

FIG. 2 shows a method for thermomechanically perforating the coated nonwoven web made using the method shown in FIG. 1 to create macroperforations therein. This second aperturing step involves passing the coated microperforated nonwoven web under a perforating force delivered by subjecting the web to raised protuberances or pins and applying a balanced thermomechanical contact perforation pressure to create macroperforations therein that extend through at least the polyethylene coating. The thermomechanical perforating step may be achieved by inserting the extrusion coated web between a set of perforating rolls that have on at least one of the cylinder surfaces a raised patterned texture, such as an engraving pattern or individual needles, that can perforate the coating by exerting pressure and, when necessary, heat against the area of the web that is in contact with the raised areas of the engraved cylinder. A matched counter rotating cylinder made of engraved steel, rubber or cardboard may have matching receptacles for the raised areas.

As shown in FIG. 2, the microperforated nonwoven web 10 is fed through perforating calendar rolls 16 and 18 under pressure to create macroperforations 22 that extend through at least the polyethylene coating 2 of the web. The macroperforations typically are elliptical in shape and typically extend through both the polyethylene coating and the nonwoven web. The macroperforations have a density of between about 6 and about 35 perforations per linear inch, typically between about 8 and about 25 perforations per linear inch. One calendar roll, such as roll 16, has protruding perforating surfaces 20 and the other calendar roll, such as roll 18, has a surface that is either smooth or has receptacles for the protruding surfaces of roll 16. Roll 18 can be heated, typically to about 300° F. (about 148.9° C.), or cooled and can be either driven by the roll 16 or self-driven in a direction that facilitates the formation of apertures. In another example, the nonwoven web is fed through a nip of heated pins and a counter rotating brush roll. In such a case, the pins perforate the web. After the perforating is completed, the nonwoven web 14 can be wound on a roll and shipped to customers for use in the desired product applications.

Figure 3:
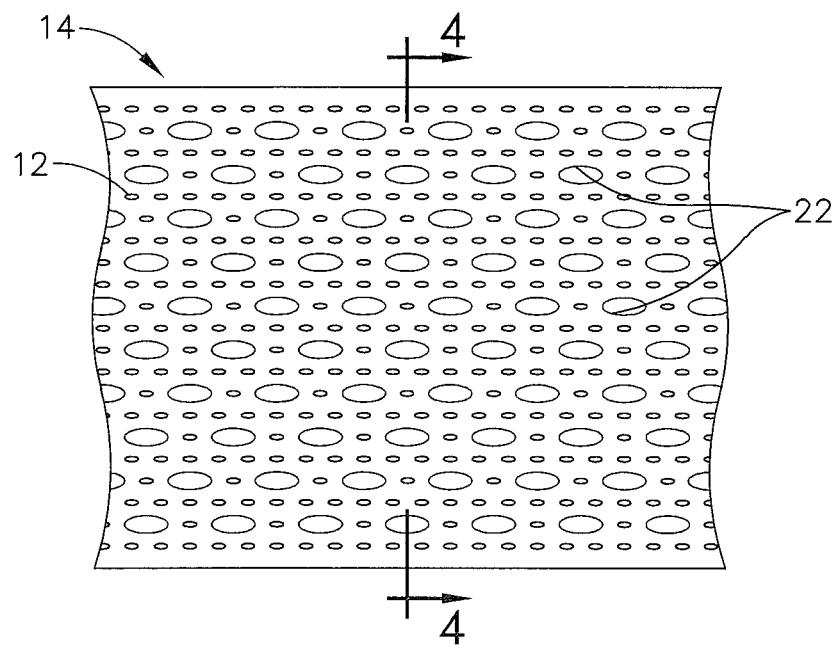
FIG. 3 shows a top view of a perforated nonwoven web of the invention made using the methods shown in FIGS. 1 and 2.
Figure 4:
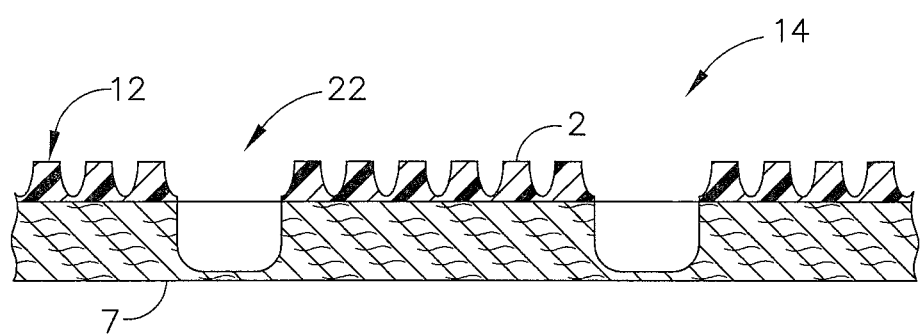
FIG. 4 is an enlarged sectional view of a portion of the perforated nonwoven web of FIG. 3.

FIG. 3 is top view from the wearer side of the perforated nonwoven web 14 of the invention made using the methods of FIGS. 1 and 2, and showing the microperforations 12 and macroperforations 22 therein. As described above, the polyethylene coating layer may have a side A that is more suitable for perforation and a side B that is more suitable for attachment to the nonwoven web. In one embodiment, the macroscopically expanded nonwoven web has raised funnel-like perforations, which typically face the side of the wearer.

In another embodiment, the perforation device has raised needles that are used to expand the nonwoven web in the lower plane that faces the absorbent core of an absorbent article. The perforating roller device is typically heated to a temperature close to, or lower than, the softening point of the nonwoven web, usually greater than 70° C. but less than 200° C., and generates perforations as a result of a combination of pressure and heat. The resultant web, such as web 14 shown in FIG. 3, has the ability to absorb fluid from both the raised microperforations 12 and macroperforations 22. The large, deep macroperforations absorb the largest amount of the fluid, and the microperforations act as a capillary buffer that absorbs any remaining fluid near the wearer skin and prevents the nonwoven web from sticking to the skin.

It may be desired in certain embodiments to treat various areas of the perforated nonwoven web differently to provide visually different structures with more than one microtexture shape and/or macrotexture shape. For example, macroperforation patterns may be interposed, or the screen of the extrusion coating may have different patterns on its surface.

Different perforation needle or raised embossing patterns may provide for varying sizes or shapes of macroscopic embossing. Various macroperforations and microtextured nonwovens may be used, in whole or part, to provide topsheets for various types of absorbent articles, including adult, child or infant incontinence products (for example, diapers, briefs, etc.), feminine hygiene products (for example, menstrual products, sanitary napkins, pantiliners, etc.), wraps, and sterile and non-sterile bandages, with and without absorbent sections. The nonwoven webs of the invention are also useful in other disposable and/or multiple use products, including garments, apparel, undergarments, undershirts, bras, briefs, panties, bathing suits, coveralls, socks, head coverings and bands, hats, mitten and glove liners, medical clothing, bed sheets, medical drapes, packaging materials, protective covers, household and office products, and medical or therapeutic devices and wraps.

Further treatment may also be desired, such as application of a lotion or semi-curable nanofiber to the macroscopically created embossing zones. Mechanical activation processes can be used to alter the shape of the apertures and the distance between the embossing zones and the rest of the apertures.

The nonwoven webs herein may also be combined with other components to form laminate or composite materials, finished and semi-finished, which may be further treated through embossing, perforating, sewing, bonding, printing, cutting, shaping, gluing, fluting and/or sterilizing processes known in the art.

In one example of the invention, a molten polyethylene A/B blend, with the A layer comprising by weight about 88% LDPE, 8% calcium carbonate and 4% LLDPE and the B layer comprising about 88% LDPE and 12% EVA (ethylene vinyl alcohol), having a basis weight of about 15 gsm, is extruded using a co-extrusion vacuum lamination line onto a carded thermobonded polypropylene nonwoven web having a basis weight of 16 gsm, available from Shalag Shamir Corporation, as the nonwoven web with molten coating on its surface contacts a 52 Mesh forming screen available from Stork Corporation Netherland. A pneumatic differential pressure is applied forcing the polyethylene coating to mold and creating microperforations in the coating at a density of about 52 microperforations per linear inch. Almost at the same time as the polyethylene coating is perforated, it gets strongly and continuously attached to the nonwoven web, as shown in FIG. 1. Once the polyethylene coating begins to crystallize, the microperforated coated nonwoven web is subjected to a second thermomechanical perforation step by feeding it through perforating rolls, such as shown in FIG. 2, one of which has raised elliptical dagger-shaped needles. The needles have a density of 8 per linear inch and are elliptically shaped to help retain the flexibility of the web. A counter roll made of smooth rubber is used to insure that the macroperforations extend through the polyethylene coating layer and the nonwoven web. Such a perforation unit is available from several suppliers, including Burckhardt AG in Basel, Switzerland. After the nonwoven web exits the needle perforation nip, it is wound on a roll and later shipped to the customer for use as a topsheet on an absorbent article.

Although the present invention has been described with respect to specific embodiments, various modifications will be apparent from the present disclosure and are intended to be within the scope of the following claims.

What is claimed is:

1. An extrusion coated, perforated nonwoven web, said nonwoven web made by:
    (a) extruding a molten polyethylene coating having a basis weight between about 7 and about 17 gsm onto a nonwoven web having a basis weight between about 9 and about 40 gsm;
    (b) while aperturing said molten polyethylene coating through heat and pneumatic pressure differential to create raised conical microperforations therein at a density of between about 35 and about 120 perforations per linear inch to provide a microperforated nonwoven web; and then
    (c) thermomechanically perforating said microperforated nonwoven web by feeding it through perforating rolls that contact the nonwoven web, at least one of said perforating rolls having raised protuberances to create macroperforations therein that extend through at least the polyethylene coating, said macroperforations having a density of between about 6 and about 35 perforations per linear inch, wherein said microperforations and said macroperforations are capable of absorbing and transporting liquid.

2. The extrusion coated, perforated nonwoven web of claim 1 wherein the polyethylene coating has a basis weight between about 10 and about 15 gsm.

3. The extrusion coated, perforated nonwoven web of claim 1 wherein the polyethylene coating comprises a co-extruded polymeric blend and inorganic filler particles.

4. The extrusion coated, perforated nonwoven web of claim 1 wherein the microperforations have a density of between about 45 and about 80 perforations per linear inch.

5. The extrusion coated, perforated nonwoven web of claim 1 wherein the macroperforations are elliptical in shape and extend through both the polyethylene coating and the nonwoven web.

6. The extrusion coated, perforated nonwoven web of claim 1 wherein the macroperforations have a density of between about 8 and about 25 perforations per linear inch.

7. The extrusion coated, perforated nonwoven web of claim 6 wherein the macroperforations are elliptical in shape and extend through both the polyethylene coating and the nonwoven web.

8. The extrusion coated, perforated nonwoven web of claim 7 wherein the microperforations have a density of between about 45 and about 80 perforations per linear inch.

9. The extrusion coated, perforated nonwoven web of claim 8 wherein the polyethylene coating comprises a co-extruded polymeric blend and inorganic filler particles.

10. The extrusion coated, perforated nonwoven web of claim 9 wherein the polyethylene coating has a basis weight between about 10 and about 15 gsm.

11. An absorbent article comprising an absorbent structure in liquid communication with a topsheet made of the perforated nonwoven web of claim 1.

12. An extrusion coated, perforated nonwoven web, said nonwoven web made by:

(a) extruding a molten polyethylene coating having a basis weight between about 10 and about 15 gsm onto a nonwoven web having a basis weight between about 9 and about 40 gsm;

(b) while aperturing said molten polyethylene coating through heat and pneumatic pressure differential to create raised conical microperforations therein at a density of between about 45 and about 80 perforations per linear inch to provide a microperforated nonwoven web; and then (c) thermomechanically perforating said microperforated nonwoven web by feeding it through perforating rolls that contact the nonwoven web, at least one of said perforating rolls having raised protuberances to create macroperforations therein that extend through at least the polyethylene coating, said macroperforations having a density of between about 8 and about 25 perforations per linear inch, wherein said microperforations and said macroperforations are capable of absorbing and transporting liquid.

13. The extrusion coated, perforated nonwoven web of claim 12 wherein the polyethylene coating comprises a co-extruded polymeric blend and inorganic filler particles.

14. The extrusion coated, perforated nonwoven web of claim 13 wherein the macroperforations are elliptical in shape and extend through both the polyethylene coating and the nonwoven web.

* * * * *